US00PP33704P2

(12) United States Plant Patent
Smith

(10) Patent No.: US PP33,704 P2
(45) Date of Patent: Nov. 30, 2021

(54) ***CHRYSANTHEMUM* PLANT NAMED 'CIFZ0086'**

(50) Latin Name: ***Chrysanthemum* x *morifolium***
Varietal Denomination: CIFZ0086

(71) Applicant: SYNGENTA CROP PROTECTION AG, Basel (CH)

(72) Inventor: Mark A. Smith, Alva, FL (US)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 17/232,302

(22) Filed: Apr. 16, 2021

(51) Int. Cl.
*A01H 6/14* (2018.01)
*A01H 5/02* (2018.01)

(52) U.S. Cl.
USPC ..... Plt./298

(58) Field of Classification Search
USPC ..... Plt./298, 286
See application file for complete search history.

*Primary Examiner* — Annette H Para
(74) *Attorney, Agent, or Firm* — Dale Skalla

(57) ABSTRACT

A new garden type *Chrysanthemum* plant named 'CIFZ0086' particularly distinguished by its medium size plant with round plant habit, a medium to large size daisy, scarlet red flower color and a natural season response in early October.

1 Drawing Sheet

Figure 1:
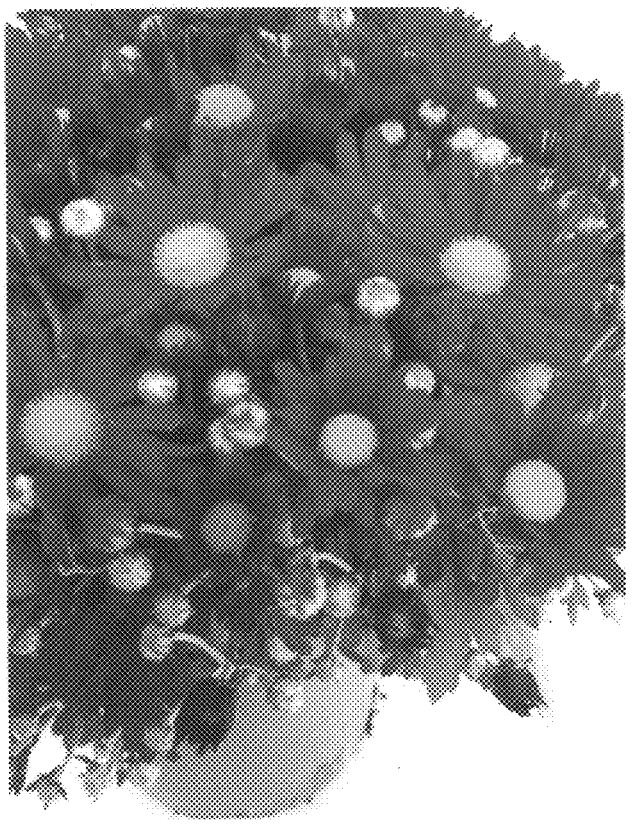

Latin name of the genus and species of the plant claimed: *Chrysanthemum* x *morifolium*.

Varietal denomination: 'CIFZ0086'.

BACKGROUND OF THE NEW PLANT

The present invention comprises a new *Chrysanthemum*, botanically known as *Chrysanthemum* x *morifolium*, and hereinafter referred to by the variety name 'CIFZ0086'.

'CIFZ0086' is a product of a planned breeding program. The new cultivar has medium size plant with round plant habit, a medium to large size daisy flowers, scarlet red flower color and a natural season response early October 'CIFZ0086' originated from a cross made in April 2016 in Enkhuizen, The Netherlands. Seeds were sown in June 2016 in Gilroy, Calif. and 'CIFZ0086' was selected from the resulting population on Nov. 13, 2016 in Alva, Fla.

The female parent was the variety 'CIFZ0066', U.S. Plant Pat. No. 30,677.

TABLE 1

Characteristics of the female parent, compared to 'CIFZ0086':

| Trait | 'CIFZ0086' | 'CIFZ0066', U.S. Plant Pat. No. 30,677 |
|---|---|---|
| Natural response: | 1 week slower | 1 week faster |
| Blackcloth response: | ½ week slower | ½ week faster |
| Flower size: | Similar | Similar |
| Flower color: | Red | Dark Pink/Purple |
| Flower type: | Similar but less ray petals | Similar but more ray petals |
| Plant size: | Smaller | Larger |
| Plant habit: | Similar | Similar |
| Flower longevity: | 15% Shorter | 15% Longer |

The male parent was 'Syeda Redda', U.S. Plant Pat. No. 22,835.

TABLE 2

Characteristics of the male parent, compared to 'CIFZ0086':

| Trait | 'CIFZ0086' | 'Syeda Redda', U.S. Plant Pat. No. 22,835 |
|---|---|---|
| Natural response: | Similar | Similar |
| Blackcloth response: | 1 week slower | 1 week faster |
| Flower size: | Similar | Similar |
| Flower color: | Lighter red, orangey red | Darker red, purple-red |
| Flower type: | Similar | Similar |
| Plant size: | Larger | Smaller |
| Plant habit: | Similar | Similar |
| Flower longevity: | 20% Longer | 20% Shorter |
| Plant strength: | Stronger | Weaker |

The first act of asexual reproduction of 'CIFZ0086' was accomplished when vegetative stem cuttings were propagated from the initial selection in January 2017 in Alva, Fla.

BRIEF SUMMARY OF INVENTION

Horticultural examination of plants grown from cuttings of the plant initiated in January 2017 and continuing thereafter, has demonstrated that the combination of characteristics as herein disclosed for 'CIFZ0086' are firmly fixed and are retained through successive generations of asexual reproduction.

'CIFZ0086' has not been observed under all possible environmental conditions. The phenotype may vary significantly with variations in environment such as temperature, light intensity and day length.

A Plant Breeder's Right for this cultivar has not yet been applied for. 'CIFZ0086' has not been made publicly available prior to the effective filing date of this application, notwithstanding any disclosure that may have been made less than one year prior to the effective filing date of this application by the inventor or another who obtained 'CIFZ0086' directly from the inventor.

The following traits have been repeatedly observed and are determined to be basic characteristics of the new variety. The combination of these characteristics distinguishes this *Chrysanthemum* as a new and distinct variety.

BRIEF DESCRIPTION OF THE PHOTOGRAPHS

The accompanying photographic drawing shows typical flower and foliage characteristics of 'CIFZ0086' with colors being as true as possible with an illustration of this type.

Figure 2:
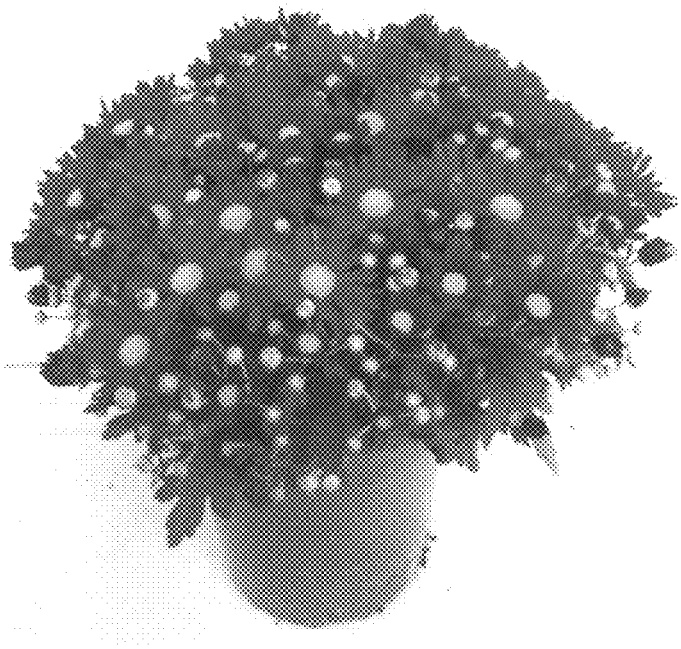

The photographic drawing shows in FIG. 1 a close view of flower of the new variety and in FIG. 2 a flowering plant from an outdoor trial.

The aforementioned photographs: FIG. 1, as well as FIG. 2 were taken in September 2020 both showing a plant from the same blackcloth outdoor trial in Enkhuizen, The Netherlands.

These plants were about 12 weeks of age. One rooted cutting per pot had been planted in a 19 cm pot, not pinched in week 24, and black clothed from week 29. Plants started flowering the end of August.

DETAILED BOTANICAL DESCRIPTION

The measurements were taken in Gilroy, Calif. in September 2020 on the plants from the aforementioned trial.

Color references are made to The Royal Horticultural Society Colour Chart (R.H.S.) 2001.

DIFFERENCES BETWEEN THE NEW VARIETY 'CIFZ0086' AND A MOST SIMILAR VARIETY

TABLE 3

| Trait | 'CIFZ0086' | 'Fame Red', Unpatented |
|---|---|---|
| Natural response: | 1.5 weeks slower | 1.5 weeks faster |
| Blackcloth response: | 1.5 weeks slower | 1.5 weeks faster |
| Flower size: | Larger | Smaller |
| Flower color: | Similar | Similar |
| Flower type: | Similar | Similar |
| Plant size: | Larger | Smaller |
| Plant habit: | Similar | Similar |
| Flower longevity: | 30% Longer | 30% Shorter |
| Flowering uniformity: | More uniform flowering | Less uniform flowering |

Plant:

*Form, growth and habit.*—Herbaceous garden-type, stems. Upright and outwardly spreading, freely branching, strong and moderately vigorous growth habit.

*Plant height (above soil).*—14 cm.

*Plant height (inflorescence included).*—18 cm.

*Plant width.*—34 cm.

Roots:

*Number of days to initiate roots.*—About 4 days at about 22° C.

*Number of days to produce a rooted cutting.*—14-16 days at 22° C.

*Type.*—Fine, fibrous, free branching.

*Color.*—RHS N155B.

Foliage:

*Arrangement.*—Alternate.

*Immature leaf, color upper surface.*—RHS 146A.

*Immature leaf, color lower surface.*—RHS 147B.

*Mature leaf, color, upper surface.*—RHS 147A.

*Mature leaf, color lower surface.*—RHS 147B.

*Length.*—4.7 cm.

*Width.*—3.6 cm.

*Shape.*—Ovate, with distinct lobes.

*Base shape.*—Attenuate.

*Apex shape.*—Mucronate.

*Margin.*—5-lobed (palmate), edge dentate.

*Number of margin indentations.*—Medium.

*Depth of margin indentations.*—Medium.

*Leaf length terminal lobe relative to total leaf length.*—Medium.

*Leaf depth lower lateral sinus.*—Shallow.

*Texture, upper surface.*—Bifid hairs.

*Texture, lower surface.*—Bifid hairs.

*Color of veins, upper surface.*—RHS 148B.

*Color of veins, lower surface.*—RHS 148B.

*Pattern of veining.*—Palmate.

*Petiole color.*—RHS 148B.

*Petiole length.*—1.6 cm.

*Diameter.*—0.3 cm.

*Texture.*—Bifid hairs.

*Presence of stipules.*—Yes.

*If present, size of stipules.*—Small.

Stem:

*Quantity of main branches per plant.*—6-8.

*Color of stem.*—RHS 147B.

*Length of stem.*—12 cm.

*Diameter.*—0.5 cm.

*Length of internodes.*—0.8-2.4 cm.

*Texture.*—Bifid hairs.

*Color of peduncle.*—RHS 147B.

*Length of peduncle.*—4.0 cm.

*Peduncle diameter.*—0.3 cm.

*Texture.*—Bifid hairs.

Inflorescence:

*Type.*—Compositae, solitary, daisy-type inflorescences borne terminally above foliage, ligulate ray florets arranged acropetally on a capitulum giving a single flower.

*Quantity of short days to flowering (response time).*—Approximately 8 weeks.

*Natural season flowering.*—Early October.

*Quantity of inflorescences per plant.*—130-150 with many small buds developing.

*Lastingness of individual blooms on the plant.*—About five weeks from first color.

*Fragrance.*—Spicy.

Bud (when showing color):

*Color.*—RHS 53A.

*Length.*—0.9 cm.

*Width.*—0.9 cm.

*Shape.*—Oblate.

Immature inflorescence (at moment of opening):

*Diameter.*—1.5 cm.

*Color of ray florets, upper surface.*—RHS 53A.

*Color of ray florets, lower surface.*—RHS 53A.

Mature inflorescence:

*Diameter.*—4.7 cm.

*Depth.*—0.5 cm.

*Total diameter of disc.*—1.3 cm.

*Receptacle color.*—RHS 147B.

*Receptacle height.*—0.4 cm.

*Receptacle diameter.*—1.4 cm.

*Length of corolla tube.*—Short.

Ray florets:
*Average quantity of florets.*—30-35 in two whorls.
*Color of florets, upper surface.*—RHS 53A.
*Color lower surface.*—RHS 9A.
*Length.*—2.5 cm.
*Width/diameter.*—0.6 cm.
*Shape.*—Elliptical.
*Apex shape.*—Mostly obtuse and dentate.
*Base shape.*—Tube.
*Margin.*—Entire, Small incisions may be present at tip.
*Margin: type of rolling.*—Weakly involute.
*Texture, upper surface.*—Papillate.
*Lower surface.*—Papillate.
*Ribs present.*—No.
*Number of keels.*—0.
*Profile at widest point.*—Weakly convex.
*Longitudional axis shape.*—Reflexing.

Disc florets:
*Number of disc florets.*—Up to 350.
*Width.*—0.1 cm.
*Length.*—1.0 cm.
*Color.*—RHS 17B; RHS 145D at base.

Inflorescence (at moment of senescence):
*Color of ray florets, upper surface.*—RHS 53A.
*Color of ray florets, lower surface.*—RHS 53B.

Phyllaries:
*Quantity.*—20-25.
*Color, upper surface.*—RHS 147B.
*Color, lower surface.*—RHS 147B.
*Length.*—0.8 cm.
*Width.*—0.1-0.2 cm.
*Shape.*—Lanceolate.
*Apex shape.*—Acute.
*Base.*—Fused.
*Margins.*—Entire.
*Texture, upper surface.*—Glabrous.
*Texture, lower surface.*—Canescent.

Reproductive organs:
*Pistil.*—One.
*Length.*—0.4 cm.
*Style color.*—RHS 150B.
*Style length.*—0.3 cm.
*Stigma color.*—RHS 8B.
*Stigma shape.*—Bi-parted.
*Ovary color.*—RHS 145D.
*Ovary length.*—0.3 cm.
*Ovary width.*—0.1 cm.

Androecium:
*Stamens.*—1, found on only disc florets.
*Color of filaments.*—RHS 2B.
*Length filaments.*—0.2 cm.
*Anther color.*—RHS 17B.
*Anther length.*—0.2 cm.
*Anther shape.*—Oval to club shaped.
*Color of pollen.*—RHS 17B.
*Pollen amount.*—Moderate.
*Fertility/seed set.*—Has not been determined to date.
*Disease/pest resistance.*—Has not been determined to date.
*Hardiness.*—Has not been determined to date.

What is claimed is:

1. A new and distinct variety of *Chrysanthemum* plant named 'CIFZ0086' substantially as illustrated and described herein.

* * * * *